United States Patent [19]

Kwan

[11] Patent Number: 5,384,245
[45] Date of Patent: Jan. 24, 1995

[54] STABLE, SINGLE-LIQUID ALPHA-AMYLASE REAGENT

[75] Inventor: Shing F. Kwan, Ventura, Calif.

[73] Assignee: Ivan E. Modrovich, Camarillo, Calif.

[21] Appl. No.: 878,347

[22] Filed: May 4, 1992

[51] Int. Cl.⁶ .......................... C12Q 1/40; C12N 9/96
[52] U.S. Cl. ...................... 435/22; 435/188; 435/810
[58] Field of Search ............... 424/94.2, 94.3; 435/14, 435/18, 22, 188, 201, 269, 810; 436/8, 15, 18, 164, 811

[56] References Cited

U.S. PATENT DOCUMENTS

| | | | |
|---|---|---|---|
| 4,310,625 | 1/1982 | Modrovich | 435/15 |
| 4,550,077 | 10/1985 | Woodbridge | 435/22 |
| 4,649,108 | 3/1987 | Blair | 435/22 |

FOREIGN PATENT DOCUMENTS 0085348 8/1983 European Pat. Off. .

OTHER PUBLICATIONS

Back, J., Increased Thermal Stability of Proteins . . . Biochemistry V 18 (23) 1979, pp. 5191–5196.

*Primary Examiner*—Michael G. Wityshyn
*Assistant Examiner*—Ralph Gitomer
*Attorney, Agent, or Firm*—Christie, Parker & Hale

[57] ABSTRACT

In a single liquid alpha-amylase reagent composition comprising an aqueous solution of at least one substrate which is hydrolyzed when mixed with a sample of body fluid containing alpha-amylase to yield a detectable label, alpha-glucosidase from *Bacillus stearothermophilus* is used to cooperate with the alpha-amylase in the formation of the detectable label and the composition being stable against degradation for a least 6 months at 2° to 10° C.

24 Claims, 1 Drawing Sheet

STABLE, SINGLE-LIQUID ALPHA-AMYLASE REAGENT

CROSS REFERENCE TO RELATED APPLICATION

This is an improvement to U.S. application Ser. No. 07/700,996 filed May 10, 1991, which is a continuation of application Ser. No. 07/074,569 filed Jul. 17, 1987, now abandoned, both incorporated herein by reference.

FIELD OF THE INVENTION

This invention relates generally to reagents for determining serum levels of alpha-amylase and, more particularly, to a stable, single-liquid alpha-amylase assay reagent.

BACKGROUND OF THE INVENTION

Alpha-amylase is found primarily in the pancreas and salivary glands. When released in the digestive tract, the enzyme hydrolyses starch. Alpha-amylase determinations are useful in the diagnosis of diseases of the pancreas and parotids. Elevated serum levels are associated with acute pancreatitis and other pancreatic disorders, as well as mumps and bacterial parotitis. Decreased serum values may be found with liver diseases, such as hepatitis and obstructive jaundice, and liver tumors or abscesses.

Historically, methods for determining alpha-amylase in serum have included viscosimetric, turbidimetric, iodometric, and reductometric technology. With these methodologies, reaction times are long, endogenous glucose tends to interfere, reaction colors are unstable, and reproducibility is poor. Recently, assay systems for the determination of alpha-amylase have been developed.

Such assay systems for alpha-amylase typically include a reagent comprising a polysaccharide or oligosaccharide substrate with a label, e.g., a chromogen unit, attached. The substrate is hydrolyzed by alpha-amylase to form one or two smaller oligosaccharides. The reagent further comprise one or more enzymes which further hydrolyze the smaller oligosaccharides to free the label unit which can then be detected spectrophotometrically.

Such assay reagents enable rapid and accurate determinations of alpha-amylase compared to historical methodologies. However, the stability of such reagents is poor. Consequently, assay reagents are generally stored in a lyophilized state and must be reconstituted prior to use. Once reconstituted, the shelf life is generally one to fourteen days. Moreover, such reagents tend to give variable and often undesirably high background levels which adversely affect the consistency and accuracy of this system.

The above-identified patent applications disclose a stable, single-liquid alpha-amylase assay reagent for the rapid determination of the alpha-amylase in biological fluids. The assay reagent comprises an aqueous solution substantially free of alpha-amylase and/or alpha-amylase activity containing at least one substrate which is cleavable directly or indirectly by alpha-amylase to produce a detectable change in the reaction mixture. The detectable change may be the production or elimination of a detectable component. Such components may be detected by any suitable means including optical, electrochemical and thermochemical means.

In a preferred embodiment of the invention, the reagent comprises a polysaccharide or long-chain oligosaccharide substrate having a label attached at the reducing end. The substrate is hydrolyzable by alpha-amylase to form short-chain oligosaccharides, at least one of which comprises the label. The reagent further comprises at least one exo-enzyme, and preferably a pair of exo-enzymes, current maltase and alpha- or beta-glucosidase, which further hydrolyses the oligosaccharides to free the label which is then detectable spectrophotometrically. The rate at which the free label is formed provides a direct indication of the concentration of alpha-amylase in the biological fluid.

The alpha-amylase reagent is made substantially free of alpha-amylase by utilizing sterile water and purified reagents, and by passing the exo-enzymes and substrate, either individually or in combination, through a filter having a pore size of not more than about 0.2 micron to remove alpha-amylase-producing bacteria. Elimination of alpha-amylase from the reagent eliminates the consumption of the substrate during storage and hence stabilizes the reagent.

The alpha-amylase assay reagent is further stabilized by the inclusion of a polyol which retards the degradation of the exo-enzymes.

In commercial reagent we have employed as the exo-enzymes a mixture of a fairly high concentration of about 10 U/ml alpha-glucosidase (maltase) derived from yeast and 10 U/ml glucoamylase.

SUMMARY OF THE INVENTION

It has now been found that alpha-glucosidase a maltase from *Bacillus Stearothermophilus* is unusually effective in exhibiting both an exo-amylase and glucosidase activity providing a high response at lower concentrations and does not require the use of a polyol to retard degradation. In consequence the exo enzyme concentration in the form of alpha glucosidase from *Bacillus Stearothermophilus* can be used in a concentration as low as about 1.5 U/ml and equal or exceed the performance of our prior compositions in linearity, response time and stability and a polyol can be eliminated from the composition. A preferred concentration is about 2.2 U/ml.

DETAILED DESCRIPTION OF THE INVENTION

Figure 1:
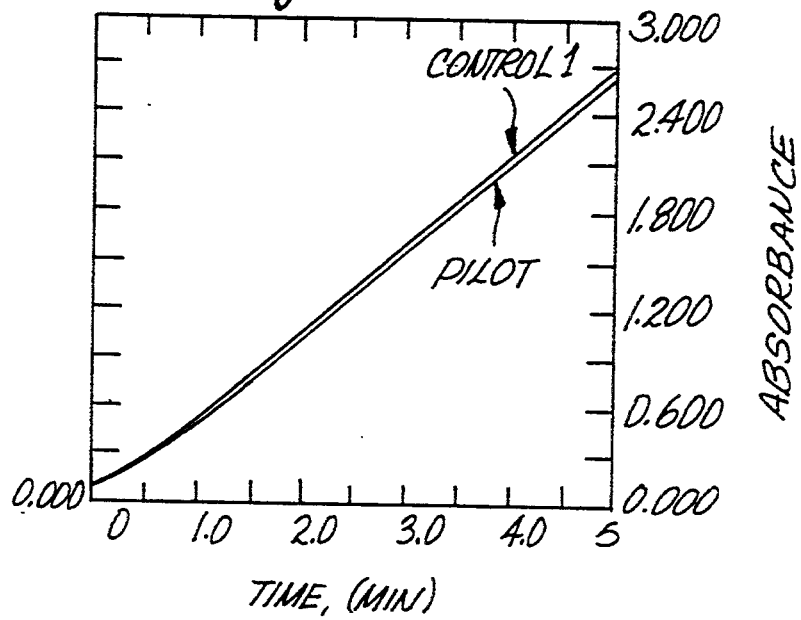
FIG. 1 is a plot of absorbance against time using the High Control which represents a worst case scenario in clinical chemistry. It establishes the composition of the instant invention (pilot) performs equal to control 1, a commercial composition containing two exoenzymes. The linearity of the pilot is established as the equivalent to control 1.

In accordance with the present invention, there is provided improved single liquid assay reagent for determining the concentration of alpha-amylase in biological fluids or sera. The assay reagent produced is a single reagent, aqueous solution that is stable for at least six months and usually for at least 18 month at about 2° to about 10° C.

As used herein, the term "stable" means that the reagent maintains at least 95% recovery. For example, if the reagent, when first mixed, provides an alpha-amylase analysis of 100 units for a particular sample, the reagent is considered "stable" if, after a select period of time, e.g. six months, the reagent provides an analysis on the same sample of at least 95 units, i.e., 95% of the original analysis.

The addition of a biological fluid containing alpha-amylase to the reagent initiates a series of reactions resulting in the production of a detectible product, the rate of production of the detectible product being directly proportional to the concentration of alpha-amylase in the biological fluid.

The assay reagent comprises a substrate which is hydrolyzable by alpha-amylase, such as a benzylidene and/or ethylidene blocked substrate and the exo-enzyme alpha-glucosidase from *Bacillus Stearothermophilus* is used in a concentration of at least about 1.5 U/ml preferably about 2.2 U/ml of assay to achieve a commercially acceptable response time in the determination of alpha amylase namely within 10 minutes at an assay temperatre of 37° C. The current source is Toyobo Co., Ltd., Osaka, Japan.

The substrate is a polysaccharide or, more preferably, an oligosaccharide which is hydrolyzed by alpha-amylase. The substrate preferably contains at least three glucose units. The reducing end glucose unit of the substrate is bonded, by a bond which can be cleaved by alpha-glucosidase, to a label which exhibits an optically measurable change upon cleavage of the bond. The terminal glucose unit of the substrate is bonded to a blocking group which inhibits cleavage by exo-enzymes of the bond between the terminal glucose unit and the adjacent glucose unit.

The label is preferably a chromophore, a fluorophore, a chemiluminescent substituent, or a bioluminescent substituent. Preferred labels include p-nitrophenol, o-nitrophenol, coumarin derivatives such as 4-methylumbelliferone and luciferin. Preferably, the substrate has eight or fewer glucose units and most preferably has six or seven. Preferred blocking substituents are acetals or ketals, e.g., benzylidene and/or ethylidene. A substrate concentration of about 2 mg/ml is presently preferred.

The alpha-glucosidase from the microbial source *Bacillus Stearothermophilus* operates and performs the dual function of yeast derived alpha-glucosidase and glucoamylase in freeing the label for detection by conventional means.

Once alpha-amylase has cleaved the 1,4-glucosidic linkage, the exo enzyme goes to work to cleave the necessary reamining linkages to finally liberate the chromophore. The rate at which the chromophore is formed is directly proportional to the amylase activity.

The exo enzyme, namely alpha glucosidase from *Bacillus Stearothermophilus*, is present in a quantity sufficient to be in excess and not be a limiting factor for the reaction. It has been found that a concentration of about 1.5 U/ml of alpha glucosidase or greater will provide a sufficient excess to meet performance and stabilty criteria, namely the total reaction time is less than 10 minutes and a reagent that remains stable for at least 6 months at about 2° C. to about 10° C. or at least about 1 day at 41° C. It is preferred that the reagent remain stable for at least 12 to 18 months at about 2° C. to about 10° C. or at least about 3 days at 41° C.

In addition to the substrate and the alpha-glucosidase, the assay reagent comprises a buffer system which provides a source of calcium, e.g., calcium chloride, and an additional source of chloride, e.g., sodium chloride. Calcium and chloride ions are required to activate the alpha-amylase. The calcium chloride and sodium chloride are present in sufficient amounts that neither the concentration of calcium nor chloride ions is rate-controlling. A calcium chloride concentration of about 5 mM and a sodium concentration of about 50 mM are presently preferred.

In the practice of the invention, the assay reagent may be stabilized by a combination of techniques. A water soluble polyol which includes diols may be optionally used to inhibit time degradation. The polyols include ethylene glycol, polyethylene glycol, glycerol, sorbitol, and mixtures thereof. The presently preferred polyol is sorbitol and is preferably used.

If employed the polyol, is maintained in the reagent in a concentration sufficient to retard the degradation of the exo-enzymes without interfering adversely with reagent utility. The concentration of polyol may be maintained in the range of to about 300 grams per liter preferably about 10 to about 300 grams per liter, more preferably about 30 to about 70 grams per liter. A preferred concentration is about 50 grams per liter. Above about 300 grams per liter, and the viscosity of the reagent tends to become undesirably high.

The alpha-glucosidase and substrates are presently further stabilized by the addition of a buffer capable of maintaining the reagent at pH of from about 6.5 to about 7.5. Preferred buffers are zwitterionic buffers such as 3-N-morpholine propane sulfonic acid (MOPS), N-2-hydroxyethylpiperazine-N'-2-ethane sulfonic acid (HEPES), tris (hydroxymethyl) methylaminopropane sulfonic acid (TAPS), or 3 (N-tris (hydroxymethyl)methylamino)-2-hydroxy propane sulfonic acid. MOPS is presently preferred.

The zwitterionic buffer is preferably present in the range of from about 0.01 to about 1.0 moles per liter, and preferably 0.05 to about 0.1 moles per liter. Concentrations of zwitterionic buffers above about 0.1 molar is not preferred as such concentrations tend to create an high ionic strength in the reagent which tends to destabilize the enzymes. Concentrations below about 0.05 molar are not preferred because the beneficial effect of the zwitterionic buffer is diminished.

It is believed that the polyol, if employed, and the zwitterionic buffers retard degradation by associating with the enzymes, thereby preventing the association of other components which act on the enzymes detrimentally. It is also believed the polyol and/or zwitterionic buffers also prevent deactivation of the enzymes by maintaining the effective 3-dimensional configuration of the enzyme.

While the alpha-glucosidase from *Bacillus Stearothermophilus* is unusually pure and free of contaminants which produce alpha-amylase so as to avoid the need for filtration, filtration through a filter sufficiently small to remove the alpha-amylase-producing microorganisms is preferably practiced to ensure the absence of alpha-amylase producing microorganisms. Filtration is preferably through a filter having a pore size no greater than about 0.2 micron.

It is understood that, in addition to filtering of enzymes and substrate, it is important that there be no contamination of alpha-amylase-producing bacteria from other sources, such as the water or equipment used in preparing the reagent. Hence, the equipment used must be sterile, e.g., autoclaved, and the water used in the reagent is distilled water or water which has been boiled.

It is also still preferred to incorporate into the reagent one or more antimicrobial agents, i.e., agents toxic to microbial contaminants or at least capable of inhibiting or retarding microbial growth. Such agents include cetyltrimethylammonium (CTMA) bromide, cobalt complexes such as [Co(NH$_3$)-4(H$_2$O)Cl] SO$_4$ and [Co(-OH) Co(NH$_3$)$_4$)$_3$] (SO$_4$)$_3$ 4H$_2$O, oyster glycogen, macrodextrin, sodium azide, thimerosal, and sodium dodecyl sulfate. The presently preferred antibiotic agents include cetyltrimethylammonium (CTMA) bromide in a concentration of about 0.001%, bacterium in an amount of about 0.075 mg/ml, and sodium azide in an amount of about one gram per liter.

In preparing the reagent, all of the components can be mixed together in a batch mixing process. However, because of the high expense of the enzymes and substrate, it is preferred to initially prepare stock solutions of the buffer, an enzyme concentrate and a substrate.

The presently preferred composition is per liter of deionized water.

| | |
|---|---|
| MOPS | 10.46 g |
| NaOH(4 molar) | 5.8 ml |
| CaCl$_2$.2H$_2$O | 1.03 g |
| NaCl | 2.92 g |
| Sorbitol | 50 g |
| Sodium Azide | 1 g |
| Brij-35 (6% Soln) | 5 ml |
| Ethylidene Blocked Substrate | 2 mg/ml |
| Alpha Glucosidase from (Bacillus Stearothermophilus) | 2.2 U/ml |
| pH | 7.0 |

Brij-35 is a polyoxyethylene (23) lauryl ether, a non-ionic detergent having a HLB value of 16.9.

The following procedure was employed in determining the utility of alpha glucosidase for Bacillus Stearothermophilus in the assay composition.

To enable a valid comparison of performance characteristics, especially recoveries of patient samples, between the different formulations, a single buffer was compounded without coupling enzymes and blocked-substrates. They were added individually. Thus pH differences were minimized.

A buffer solution was prepared by combining per liter of deionized water:

| | |
|---|---|
| 10.46 g | MOPS |
| 5.8 ml | NAOH, 4M |
| 0.74 g | EDTA, Na$_2$ |
| 1.03 g | CaCl$_2$ |
| 2.92 g | NaCl(H2O)$_2$ |
| 50 g | Sorbitol |
| 1 g | Sodium Azide (NaN$_3$) |
| 5 ml | 6% Brij-35 |
| pH to 7.0 | |

The buffer was formed with good practice but not aseptically fulled.

Three formulations were prepared. They were:
Pilot=buffer+2 mg/ml Ethylidene Blocked Substrate (Boehringer Mannheim) +2.2 U/ml Alpha-glucosidase from Bacillus Stearothermophilus supplied by Toboyo Co., Ltd, Osaka, Japan Control 1=buffer+2 mg/ml Benzylidene Blocked Substrate (Genzyme) +10 U/ml Alpha-glucosidase, yeast maltase +10 U/ml Glucoamylase Control 2=buffer+2 mg/ml Ethylidene Blocked Substrate +10 U/ml Alpha-glucosidase, yeast Maltase +10 U/ml Glucoamylase All evaluations were performed either manually on an Beckman DU70 or a Mira under the following conditions:

| | |
|---|---|
| Ratio sample to reagent = | 1:40 |
| Temperature = | 37° C. |
| High control = | Challenge amylase control at 2500 U/l |
| Amylase Controls = | Challenge at amylase current ratio of to 2500 U/l 2000–2500 U/l |
| Patient samples = | normal samples |

Lag Determination:

Using the High Control at 2500 U/l, both the Control 1 and Pilot exhibited less than a 30 second lag and a linear assay time of at least five minutes. See attach FIG. 1 for comparisons. The pilot exhibited excellent linearity and a lag phase similar to Control 1, the amylase single reagent currently sold.

Recovery

Table 1 shows a comparison of recovery against Challenge of different amylase concentrations and ten sera samples from humans.

TABLE 1

| Sample | Pilot | Control 1 | Control 2 |
|---|---|---|---|
| Challenge, 0% | 0 | 0 | 0 |
| Challenge, 20% | 508 | 500 | 514 |
| Challenge, 40% | 987 | 994 | 1001 |
| Challenge, 50% | 1259 | 1231 | 1246 |
| Challenge, 60% | 1485 | 1595 | 1480 |
| Challenge, 80% | 1960 | 1916 | 1944 |
| Challenge, 100% | 2390 | 2378 | 2427 |
| Human #1 | 55 | 51 | |
| Human #2 | 82 | 76 | |
| Human #3 | 40 | 39 | |
| Human #4 | 49 | 45 | |
| Human #5 | 29 | 30 | |
| Human #6 | 29 | 28 | |
| Human #7 | 42 | 39 | |
| Human #8 | 84 | 78 | |
| Human #9 | 66 | 63 | |
| Human #10 | 46 | 42 | |

The Pilot and controls all exhibited identical linearity. Their recoveries with Challenge dilutions are essentially identical. The Pilot appeared to have a slightly higher recovery with human sample when compared to Control 1. The alpha-glucosidase from Bacillus stearothermophilus performed the same dual function as alpha-glucosidase from yeast and glucoamylase at much lower enzyme concentration, 2.2 U/l.

Stability:

Table 2 shows change in absorbance at 405 nm after stress for 3 days at 41° C., which is equivalent to 18-month as formulated (4° C.) and storage at 4°–8° C.

TABLE 2

| | |
|---|---|
| A405, 3 days at 4° C. = | 0.061 |

TABLE 2-continued

| A405, 3 days at 41° C. = | 0.1225 |
|---|---|

Even though the pilot was compounded without autoclaved glassware and pipets, the change in absorbance was remarkably low after 3 days stress at 41° C. This is a reflection that the alpha-glucosidase from Toyobo is extremely clean (i.e., very low amylase contamination).

Stress Recoveries for the Pilot after 3 days at 41° C. in comparison to 3 days at 4° C. are shown in Table 3:

TABLE 3

| Sample, % Amylase | Temperature | |
|---|---|---|
| | 4° C. | 41° C. |
| Challenge, 0% | 0 | 0 |
| Challenge, 20% | 511 | 508 |
| Challenge, 40% | 1001 | 987 |
| Challenge, 50% | 1235 | 1271 |
| Challenge, 60% | 1518 | 1510 |
| Challenge, 80% | 1923 | 1933 |
| Challenge, 100% | 2441 | 2349 |
| Human #1 | 58 | 57 |
| Human #2 | 84 | 83 |
| Human #3 | 45 | 44 |
| Human #4 | 48 | 49 |
| Human #5 | 29 | 29 |
| Human #6 | 34 | 31 |
| Human #7 | 43 | 39 |
| Human #8 | 87 | 85 |
| Human #9 | 71 | 71 |
| Human #10 | 48 | 47 |

The 3 day, 41° C. stressed pilot recovered for all dilutions of Challenge and patient samples identical to the 4° C. reagent. The Pilot is extremely stable and resistant to stress degradation.

Lag

Figure 2:
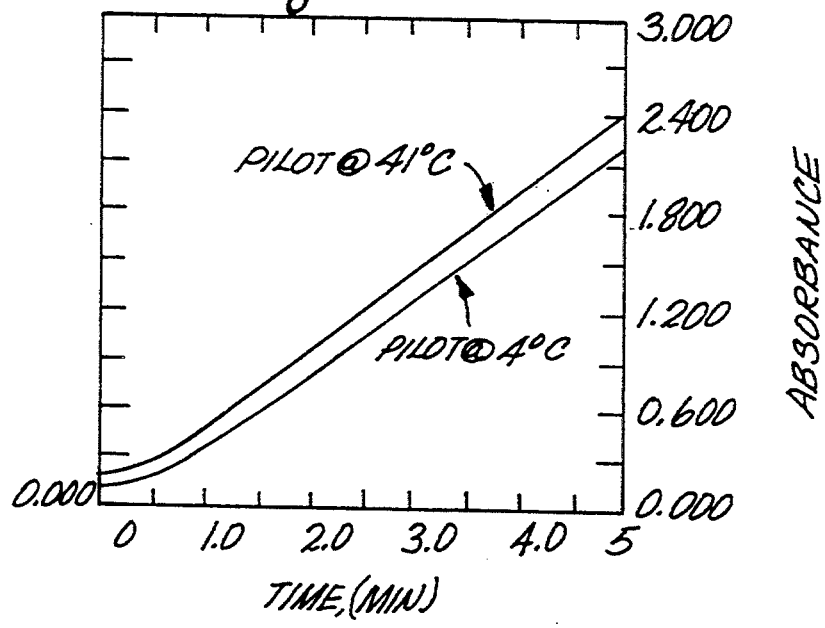
FIG. 2 is a plot of absorbance against time using High Control. It compares the composition of this invention (pilot) when refrigerated at 4° C. for 3 day to another sample of the pilot which was stressed at 41° C. for 3 days. The result establish little change in linear performance.

The lag phase and linearity of the fresh and stressed reagents were evaluated with the High Challenge sample on the Beckman DU70. The results are shown in FIG. 2. Lag time is short and linearity is excellent.

The conclusions drawn were as follows:
1. The alpha-glucosidase for *Bacillus Stearothermophilus* equals the alpha-glucosidase and glucoamylase as dual exo-enzymes.
2. An amylase single reagent can be compounded with ease employing ethylidene substrate with this single coupling enzyme.
3. Such amylase reagent performs identical to our current commercial reagent with respect to linearity, recoveries, stability, lag time, and dynamic range.
4. The reagent is a better reagent since much less coupling enzyme is introduced into the reagent matrix.

What is claimed is:

1. In a stable single liquid alpha-amylase reagent composition comprising an aqueous solution of at least one substrate which is hydrolyzed when mixed with body fluid containing alpha-amylase to yield directly or indirectly by a reaction involving alpha-amylase a detectable label released to the reaction mixture, the rate of formation of such detectable label being proportional to the amount of alpha-amylase present in the sample and at least one exo-enzyme to cooperate with the alpha-amylase in the formation of such detectable label, said substrate being present in a concentration sufficient to prevent the substrate from limiting the rate of hydrolysis thereof, said reagent composition being stable against substrate and enzyme degradation for at least 6 months at 2 to 10° C., the improvement wherein the at least one exo-enzyme comprises alpha-glucosidase from *Bacillus Stearothermophilus* in an amount sufficient to complete the assay within 10 minutes at an assay temperature of 37° C.

2. A stable, single liquid alpha-amylase reagent composition as claimed in claim 1 in which the substrate is blocked by a blocking group selected from the group consisting of benzylidene, ethylidene and mixtures thereof and in which the concentration of alpha-glucosidase in the reagent composition is at least about 1.5 U/ml.

3. A stable, single liquid alpha-amylase reagent composition as claimed in claim 1 in which the substrate is blocked by a blocking group selected from the group consisting of benzylidene, ethylidene and mixtures thereof and in which the concentration of alpha-glucosidase in the reagent composition is about 2.2 U/ml.

4. A stable, single liquid alpha-amylase reagent composition as claimed in claim 1 in which a polyol is present.

5. A stable, single liquid alpha-amylase reagent composition as claimed in claim 4 in which the polyol is selected from the group consisting of sorbitol, ethylene glycol, polyethylene glycol, glycerol and mixtures thereof.

6. A stable, single liquid alpha-amylase reagent composition as claimed in claim 2 in which a polyol is present.

7. A stable, single liquid alpha-amylase reagent composition as claimed in claim 6 in which the polyol is selected from the group consisting of sorbitol, ethylene glycol, polyethylene glycol, glycerol and mixtures thereof.

8. A stable, single liquid alpha-amylase reagent composition as claimed in claim 3 in which a polyol is present.

9. A stable, single liquid alpha-amylase reagent composition as claimed in claim 8 in which the polyol is selected from the group consisting of sorbitol, ethylene glycol, polyethylene glycol, glycerol and mixtures thereof.

10. A stable, single liquid alpha-amylase reagent comprising an aqueous solution substantially free of alpha-amylase which comprises:
(a) alpha-glucosidase from *Bacillus Stearothermophilus* present in a concentration of at least about 1.5 U/ml and sufficient to complete an amylase assay within 10 minutes at an assay temperature of 37° C.;
(b) a polysaccharide or oligosaccharide substrate for alpha-amylase having an optically detectable label bonded, by a bond cleavable by said alpha-glucosidase, to the reducing end glucose of the substrate and a blocking group bonded to the terminal end glucose of the substrate, said blocking group selected from the group consisting of ethylidene, benzylidene and mixtures thereof; and
(c) from 0 to about 300 g per liter of solution of a polyol.

11. An alpha-amylase assay reagent according to claim 10 in which the polyol is selected from the group consisting of ethylene glycol, polyethylene glycol, sorbitol, glycerol and mixtures thereof.

12. An alpha-amylase assay reagent as claimed in claim 11 in which the polyol is present in an amount of from about 10 to about 300 grams per liter of reagent.

13. An alpha-amylase assay reagent as claimed in claim 11 in which the polyol is present in the reagent composition in an amount of from about 30 to about 70 grams per liter of reagent.

14. An alpha-amylase assay reagent as claimed in claim 10 wherein a buffer is provided to maintain the reagent at a pH of from about 6.5 to about 7.5.

15. An alpha-amylase assay reagent as claimed in claim 14 wherein the buffer is a zwitterionic buffer.

16. An alpha-amylase assay reagent as claimed in claim 15 wherein the zwitterionic buffer is present in a concentration of from about 0.01 to about 1.0 moles per liter.

17. An alpha-amylase assay reagent as claimed in claim 16 wherein the zwitterionic buffer is 3-N-morpholeneproponesulfonic acid.

18. An alpha-amylase assay reagent as claimed in claim 16 further comprising at least one antimicrobial agent.

19. An alpha-amylase assay reagent as claimed in claim 18 wherein the at least one antimicrobial agent is selected from the group consisting of cetyltrimethylammonium bromine, sodium azide and mixtures thereof.

20. A stable, single liquid alpha-amylase reagent comprising an aqueous solution substantially free of alpha-amylase producing microorganisms which comprises:
(a) alpha-glucosidase from *Bacillus Stearothermophilus* present in a concentration of at least about 1.5 U/ml and sufficient to complete an alpha-amylase assay at an assay temperature of 37° C.;
(b) a polysaccharide or oligosaccharide substrate hydrolyzable by alpha-amylase and having an optically detectable label bonded, by a bond cleavable by the alpha-glucosidase, to the reducing end glucose of the substrate and a blocking group bonded to the terminal end glucose of the substrate, said substrate being present in a concentration of at least 2 mg/ml and hydrolyzed by the alpha glucosidase to yield the label at a rate proportional to the concentration of alpha-amylase in a biological fluid;
(c) from 0 to 300 grams per liter of a polyol;
(d) calcium chloride in a concentration of about 5 mM;
(e) sodium chloride in a concentration of about 50 mM; and
(f) a zwitterionic buffer sufficient to maintain to a pH of from about 6.5 to about 7.5, said reagent being stable for at least 6 months at 2° to 8° C.

21. A stable single liquid alpha-amylase reagent as claimed in claim 20 in which the blocking group is selected from the group consisting of benzylidene, ethylidene and mixtures thereof and in which the concentration of alpha-glucosidase is about 2.2 U/ml of reagent.

22. An alpha-amylase reagent as claimed in claim 20 in which the polyol is sorbitol.

23. An alpha-amylase reagent as claimed in claim 21 in which the polyol is sorbitol.

24. A stable, single liquid alpha-amylase reagent comprising an aqueous solution having a pH of about 7 and containing the following ingredients in the concentration shown:

| a) 3-N-morpholenepropane sulfuric acid | about 10.46 g/l |
| --- | --- |
| b) NaOH, 4M | about 4.8 ml/l |
| c) CaCl$_2$(H$_2$O)$_2$ | about 1.03 g/l |
| d) NaCl$_2$ | about 2.92 g/l |
| e) Sorbitol | about 50 g/l |
| f) Sodium Azide | about 1 g/l |
| g) Polyoxyethylene(23) lauryl ether (6% solution) | about 5 ml/l |
| h) Ethylidene Blocked Substrate | about 2 mg/ml |
| i) Alpha-glucosidase from *Bacillus Stearothermophilus* | about 2.2 U/ml. |

* * * * *

UNITED STATES PATENT AND TRADEMARK OFFICE
CERTIFICATE OF CORRECTION

PATENT NO. : 5,384,245
DATED : January 24, 1995
INVENTOR(S) : Shing F. Kwan

It is certified that error appears in the above-indentified patent and that said Letters Patent is hereby corrected as shown below:

Abstract, line 2, change "comprising" to -- including --.
Abstract, line 8, after "degradation for" change "a" to -- at --.

Column 1, line 43, change "comprise" to -- comprises --.

Column 2, line 57, before "to another" change "day" to -- days --.
Column 2, line 59, change "establish" to -- establishes --.

Column 3, line 1, change "month" to -- months --.
Column 3, line 25, change "temperatre" to -- temperature --.
Column 3, line 55, change "exo enzyme" to -- exo-enzyme --.
Column 3, line 56, change "reamining" to -- remaining --.
Column 3, line 59, change "exo enzyme" to -- exo-enzyme --.
Column 3, line 64, change "stabilty" to -- stability --.

Column 4, line 21, change "If employed the polyol" to -- If employed, the polyol --.
Column 4, line 45, after "create" change "an" to -- a --.

Column 5, line 41, before "HLB" change "a" to -- an --.
Column 5, line 58, change "H2O" to -- $H_2O$ --.
Column 5, line 65, change "fulled" to -- filled --.

Column 6, line 10, before "Beckman" change "an" to -- a --.
Column 6, line 26, after "See" delete "attach".

UNITED STATES PATENT AND TRADEMARK OFFICE
CERTIFICATE OF CORRECTION

PATENT NO. : 5,384,245
DATED : January 24, 1995
INVENTOR(S) : Shing F. Kwan

It is certified that error appears in the above-indentified patent and that said Letters Patent is hereby corrected as shown below:

Column 6, line 65, change "month" to -- months --.

Column 10, lines 25,26, change "concentration" to
          -- concentrations --.

Signed and Sealed this

Twenty-ninth Day of August, 1995

Attest:

BRUCE LEHMAN

*Attesting Officer*  *Commissioner of Patents and Trademarks*